(12) United States Patent
Kamezaki et al.

(10) Patent No.: US 6,228,384 B1
(45) Date of Patent: May 8, 2001

(54) CAPTURING AND DETECTING MITES USING 3-PHENOXYBENZYL CHRYSANTHEMATE

(75) Inventors: Hiroki Kamezaki; Tatsuya Kamezawa, both of Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/171,639

(22) PCT Filed: Apr. 22, 1997

(86) PCT No.: PCT/JP97/01384

§ 371 Date: Oct. 22, 1998

§ 102(e) Date: Oct. 22, 1998

(87) PCT Pub. No.: WO97/39631

PCT Pub. Date: Oct. 30, 1997

(51) Int. Cl.[7] .................................................. A01N 25/10
(52) U.S. Cl. ........................ 424/409; 424/405; 424/406; 424/407; 514/531
(58) Field of Search ..................................... 424/405–409; 514/531

(56) References Cited

U.S. PATENT DOCUMENTS

| 4,569,928 | 2/1986 | Tessier et al. . |
| 4,605,549 | 8/1986 | Carle . |
| 5,312,964 | 5/1994 | Babin et al. . |

FOREIGN PATENT DOCUMENTS 6-0142906  *  7/1985  (JP) .

OTHER PUBLICATIONS

Derwent Publications Ltd., XP–002127441, (1989).
Derwent Publications Ltd., XP–002126799, (1987).
Derwent Publications Ltd., XP002126797, (1992).

* cited by examiner

*Primary Examiner*—Neil S. Levy
(74) *Attorney, Agent, or Firm*—Browdy and Neimark

(57) ABSTRACT

Mites can be captured or detected in a convenient and positive way by using a composition containing 3-phenoxybenzyl chrysanthemate.

6 Claims, No Drawings

CAPTURING AND DETECTING MITES USING 3-PHENOXYBENZYL CHRYSANTHEMATE

The present application is a U.S. national-phase application of PCT/JP97/01384 filed Apr. 22, 1997, claiming priority from Japanese priority application No. 8-137393 filed Apr. 23, 1996.

TECHNICAL FIELD

This invention relates to a composition for capturing and detecting mites, as well as methods of capturing and detecting mites using the composition. More particularly, the invention relates to methods of capturing and detecting mites using a composition containing 3-phenoxybenzyl chrysanthemate.

BACKGROUND ART

Increasing damage is being caused by mites in house dust and this is attributable to various factors including the recent tendency of ensuring insulation of the residential environment from the ambient atmosphere and the westernization of the life style of Japanese people. While many mites are problematic, Dermatophagoides are worth particular attention since they are held as the most important allergen for infantile asthma and a topic dermatitis. Methods for controlling mites in house dust range from massive ones such as installing wooden floors, removal sofas and drying tatami mats, rugs and carpets to the treatment with chemicals which is relatively easy to perform. Conventionally applied chemicals include fenthion, fenitrothion, DDVP and permethrin, as well as 3-phenoxybenzyl chrysanthemate which is used as an active ingredient in the present invention. Another control means that is gaining popularity these days is the use of mite-proof bed spreads made of microfine fibers. However, the effectiveness of these conventional mite control means is not completely reliable since they are influenced by various factors of the residential environment. To ensure effective mite control, a certain ancillary means is necessary for checking the effectiveness of the treatment applied or determining whether it is truly necessary to perform the mite control or deciding upon the area that needs intensive control. In fact, however, the very small size of mites makes it generally difficult to know whether a certain area is infested with mites. Conventionally, the existence or density of mites in a house has been detected by the color reaction between the mite residue in house dust and an aromatic diazo compound (Japanese Patent Public Disclosure No. 135844/1985), or using a compound that develops a color upon reaction with the body fluid of a mite (Japanese Patent Public Disclosure No. 83624/1994) or by using a monoclonal antibody (Japanese Patent Public Disclosure No. 207892/1993). However, these and other conventional methods of mite control have various problems such as reacting not only with a living mite but also with a dead mite, reacting with both mites and other organisms, requiring special equipment or involving cumbersome operations. Thus, there has been no convenient and positive method that allows for specific reaction with living mites.

DISCLOSURE OF INVENTION

Under these circumstances, the present inventors made intensive studies to develop a convenient and positive method of capturing mites, as well as a method of detecting mites using said method. As a result, they found that treating a mite-infested indoor environment with a composition containing 3-phenoxybenzyl chrysanthemate provided a positive and rapid way to have mites crawl out to the surface of that environment. The inventors also found that these methods enabled mites to be captured and detected in a convenient and positive manner. The present invention has been accomplished on the basis of these findings.

Briefly, the present invention provides a composition for capturing and detecting mites characterized by containing 3-phenoxybenzyl chrysanthemate as an active ingredient. The invention also provides a method of capturing mites characterized by treating a mite-infested indoor environment with a composition containing 3-phenoxybenzyl chrysanthemate and trapping the mites that have moved to the surface of that environment. The invention also provides a method of detecting mites characterized by checking for the existence of mites and determining their density after capturing them by the aforementioned method.

As already mentioned, 3-phenoxybenzyl chrysanthemate to be used in the invention is known as an active ingredient of mite control agents. However, its use has been exclusively based on its ability to kill, control the population growth of or repel mites and it has never been used with a view to capturing mites alive as accomplished by the present invention. As will be verified in the Example to be given later in this specification, the effectiveness in causing mites to crawl out to the surface area so that they can be captured alive is exhibited by the 3-phenoxybenzyl chrysanthemate of the invention in a much more salient way than other known mite control agents and, hence, is unique to this 3-phenoxybenzyl chrysanthemate.

The effectiveness of the present invention in having mites crawl out to the surface area is entirely different from the mite repelling effect. Under the repelling effect, mites will get around or move away from the chemical-treated areas of mite-favored environments such as tatami mats, rugs, carpets and futon. In the present invention, mites are forced to crawl out of the chemical-treated areas of mite-infested environments such as tatami mats, rugs, carpets and futon so that they appear on the surface. It should also be noted that the population growth control effect of the existing mite control agents develops in several days to several weeks after treatment with such agents; on the other hand, the effectiveness of the present invention in having mites crawl out to the surface area develops in only a few minutes after treatment (see Table 1 to be given later in this specification.)

BEST MODE FOR CARRYING OUT THE INVENTION

When the composition of the invention is to be applied in practice for capturing mites, the active ingredient 3-phenoxybenzyl chrysanthemate may be dusted on its own without addition of any other ingredients. If desired, it may be mixed appropriately with various vehicles and adjuvants commonly used in either a solid, liquid or gaseous form in formulating chemicals, as well as feeds, thereby preparing oil sprays, emulsifiable concentrates, dusts, granules, wettable powders, aerosols, sheets, and so forth. While 3-phenoxybenzyl chrysanthemate occurs in a plurality of isomers, all of them and any mixtures of them are included within the scope of the present invention.

The mites crawling out to the surface area can be trapped by suction, picking up, adhesion and any other known trapping techniques. However, considering the need to detect the existence and density of mites in the subsequent step, the use of an adhesive material is preferred.

If the composition of the invention is preliminarily combined with an adhesive substrate or if an adhesive material is preliminarily incorporated in the composition of the invention, mites can be forced to crawl out to the surface and captured at the same time. In this case, 3-phenoxybenzyl chrysanthemate and an adhesive material may be applied to a substrate to form a sheet, paper, film or the like that have an adhesive layer. Alternatively, the composition of the invention may be sprayed or coated onto the substrate just prior to use so that the mites crawling out to the surface can be captured. The adhesive material that can be used in the invention is not limited to any particular type and any materials to which mites get stuck to be captured may be employed.

A broader spectrum of effects can be achieved by using the composition of the invention in admixture with various kinds of attractant, acaricide, insecticide, flavors and so forth.

After capturing mites with the composition of the invention, one can check for their existence and determine their density in a convenient and positive way by examination with a magnifying glass, an optical microscope or some other suitable detecting means. Detection can also be made by combining this method with known mite detecting techniques such as a color reaction.

All mites living in house dust can be captured and detected by the methods of the invention and they will exhibit an outstanding effect on *D. farinae, D. pteronyssinus, T. putrescentiae, Cheyletus malaccensis, Chelacaropsis moorei*, and so forth.

The method of the invention is applicable to all indoor environments that are infested with mites such as rugs, carpets, sofas and various kinds of mats.

EXAMPLE

The following tests are provided for the purpose of further illustrating the present invention but are in no way to be taken as limiting.
Test 1
(Method)

A thousand mites (*D. farinae*) were let loose on pieces of nylon rug cut to a size of 10×16 cm. A culture medium (1 g) for the mites was also placed on each piece of rug. One week later, talc containing 0.35% of 3-phenoxybenzyl(±)-cis-trans-chrysanthemate was uniformly dusted over each piece of rug in such an amount that the dose of the active ingredient would be 70 mg/M$^2$. After the treatment, the number of mites that crawled out to the surface of the rug was counted over time and compared with the initial value. For counting the mites that crawled out, a stereoscopic microscope was used and in a visual field of ×10, the number of living mites that were observed on the surface of the rug for one minute was counted three consecutive times after a specified time had passed and the average was calculated. Each test was run in duplicate. Tests were conducted in the same manner using the following compounds as controls: 3-phenoxybenzyl(1RS, 3RS; 1RS, 3SR)-3-(2,2-dichlorovinyl)-2,2-dimethyl cyclopropanecarboxylate (permethrin); (RS)-2-methyl-4-oxo-3-prop-2-ynyl-cyclopento-2-enyl(±)-cis-trans-chrysanthemate (prallethrin); 5-benzyl-3-furylmethyl(+)-trans-chrysanthemate (bioresmethrin); 3,4,5,6-tetrahydrophthalimidomethyl(+)-cis-trans-chrysanthemate (d-tetramethrin); and (RS)-3-allyl-2-methyl-4-oxocyclopento-2-enyl(+)-trans-chrysanthemate (bioallethrin). The results are shown in Table 1 below.

(Results)

TABLE 1

No. of Mites Crawling Out to the Surface of Rug

| | | | Time (min) After Treatment | | | |
|---|---|---|---|---|---|---|
| | | Initial | 15 | 30 | 60 | 120 |
| Composition of the Invention | Average for the 1st run | 15.3 | 99.7 | 87.7 | 66.7 | 50.3 |
| | Average for the 2nd run | 12.7 | 80.7 | 74.3 | 51.3 | 42.3 |
| Control Composition 1 | Average for the 1st run | 5.0 | 10.0 | 10.3 | 15.3 | 9.3 |
| | Average for the 2nd run | 11.0 | 9.7 | 16.3 | 26.0 | |
| Control Composition 2 | Average for the 1st run | 10.3 | 17.7 | 10.3 | 9.3 | 10.3 |
| | Average for the 2nd run | 13.0 | 34.7 | 25.7 | 17.3 | 14.7 |
| Control Composition 3 | Average for the 1st run | 9.7 | 28.0 | 29.7 | 23.0 | 21.3 |
| | Average for the 2nd run | 7.0 | 24.3 | 18.3 | 19.7 | 15.3 |
| Control Composition 4 | Average for the 1st run | 11.3 | 32.0 | 24.0 | 32.7 | 27.7 |
| | Average for the 2nd run | 6.3 | 41.7 | 25.3 | 29.3 | 41.0 |
| Control Composition 5 | Average for the 1st run | 18.3 | 44.0 | 40.3 | 18.0 | 14.3 |
| | Average for the 2nd run | 18.0 | 45.0 | 27.3 | 14.3 | 23.7 |

(Notes)
1. The composition of the invention contained 0.35% of 3-phenoxybonzyl(±)-cis-trans-chrysanthemate.
2. Control composition 1 contained 0.35% of 3-phenoxybenzyl (1RS, 3RS; 1RS, 3SR)-3-(2,2-dichlorovinyl)-2,2-dimethylcyclopropanecarboxylate (permethrin).
3. Control composition 2 contained 0.35% of (RS)-2-methyl-4-oxo-3-prop-2-ynylcyclopento-2-enyl(±)-cis-trans-chrysanthemate (pralethrin).
4. Control composition 3 contained 0.35% of 5-benzyl-3-furylmethyl(±)-trans-chrysanthemate (bioresmethrin).
5. Control composition 4 contained 0.35% of 3,4,5,6-tetrahydrophthalimidomethyl(±)-cis-trans-chrysanthemate (d-tetramethrin).
6. Control composition 5 contained 0.35% of (RS)-3-allyl2-methyl-4-oxocyclopento-2-enyl(+)-trans-chrysanthemate (bioallethrin).

(Discussion)

As is clear from Table 1, the composition of the invention, when applied to rug, could force the mites to crawl out to the surface of the rug in a more rapid and positive way than any of the control compositions. It is generally known that the active ingredient of the composition of the invention is not very much different in mite control effect from the active ingredient of any of the control compositions used but the difference in the capability of forcing mites to crawl out to the surface of the rug was marked. It may well be said that the mite control effect is not necessarily related to the capability of forcing mites to crawl out to the surface of the rug. One may therefore conclude that the composition of the invention is a useful mite catcher.
Test 2
(Method)

A hundred mites (*D. farinae*) were let loose on pieces of nylon rug cut to a square size of 6×6 cm (except that each corner was cut off at a distance of 1 cm to give an area of 34 cm$^2$). A culture medium (100 mg) for the mites was also placed on each piece of rug, which was then placed in a glass Petri dish 9 cm in diameter. In order to evaluate how many mites would escape from the rug, the periphery of each Petri dish was coated with a band of an adhesive "TANGLE FOOT" (manufactured by Fuji Chemical Industries, Ltd. under the trade name "FUJI TANGLE"). An adhesive sheet of the same size as the rug was provided and talc containing 0.35% of 3-phenoxybenzyl(±)-cis-trans-chrysanthemate was uniformly dusted over the adhesive layer of the sheet in such an amount that the dose of the active ingredient would be 70 mg/m$^2$. The thus treated adhesive sheet was attached to the surface of the rug three days after inoculation with the mites. After 20 hours of standing, the number of mites adhering to the adhesive sheet (simply referred to as "sheet adhering mites") was counted with the aid of a stereoscopic microscope. Also counted were the number of mites on the surface of the rug (simply referred to as "on-surface mites") and the number of mites in the adhesive "TANGLE FOOT" (simply referred to as "escaping mites") and comparison was made with the initial values. As a control, an adhesive sheet treated with talc containing no active ingredient was subjected to the same test. The results are shown in Table 2 below.

(Result)

TABLE 2

Nos. of On-Surface, Escaping and Sheet Adhering Mites

|  |  |  | Initial | After treatment |
|---|---|---|---|---|
| Composition of the Invention | First run |  |  |  |
|  | No. of on-surface mites |  | 18 | 5 |
|  | No. of escaping mites |  | 0 | 12 |
|  | No. of sheet adhering mites |  | — | 42 |
|  | Second run |  |  |  |
|  | No. of on-surface mites |  | 4 | 0 |
|  | No. of escaping mites |  | 0 | 20 |
|  | No. of sheet adhering mites |  | — | 46 |
| Control Composition | First run |  |  |  |
|  | No. of on-surface mites |  | 18 | 7 |
|  | No. of escaping mites |  | 0 | 2 |
|  | No. of sheet adhering mites |  | — | 19 |
|  | Second run |  |  |  |
|  | No. of on-surface mites |  | 7 | 0 |
|  | No. of escaping mites |  | 0 | 0 |
|  | No. of sheet adhering mites |  | — | 24 |

(Notes)

1. The composition of the invention contained 0.35% of 3-phenoxybenzyl(±)-cis-trans-chrysanthemate as an active ingredient.
2. The control composition did not contain said active ingredient.

(Discussion)

As is clear from the data on the "No. of sheet-adhering mites" in Table 2, the treatment with the composition of the invention achieved more efficient capturing of mites than the treatment with the control composition. The former also provided a convenient means of enabling one to check for the existence of mites and detect their density. Therefore, the composition of the invention may well be considered to be a useful mite catcher and detector.

Industrial Applicability

As described on the foregoing pages, the composition and the methods of the invention provide convenient and positive ways to capture and detect mites. This technology also helps control mites and reduce their density and hence is expected to prove very useful in the industry concerned.

What is claimed is:

1. A method of capturing live mites comprising treating a mite-infested porous substrate in an indoor environment with a composition comprising 3-phenoxybenzyl chrysanthemate as an active ingredient and a diluent or carrier, at a concentration of said active ingredient which causes mites to crawl out of said porous substrate; and trapping the mites that have moved from within the porous substrate to the surface thereof.

2. A method of capturing live mites comprising treating a mite-infested porous substrate in an indoor environment with a composition comprising 3-phenoxybenzyl chrysanthemate as an active ingredient and a diluent or carrier, at a concentration of said active ingredient which causes mites to crawl out of said porous substrate, and further comprising an adhesive material; and trapping the mites that have moved from within the porous substrate to the surface thereof.

3. A method of detecting mites characterized by capturing mites by the method according to claim 1 and checking for the existence of mites and determining their density.

4. A method of detecting mites comprising by capturing mites by the method according to claim 2 and checking for the existence of mites and determining their density.

5. The method of claim 1 wherein said porous substrate is a sofa, tatami mat, rug, carpet or futon.

6. The method of claim 2 wherein said porous substrate is a sofa, tatami mat, rug, carpet or futon.

* * * * *

UNITED STATES PATENT AND TRADEMARK OFFICE
CERTIFICATE OF CORRECTION

PATENT NO.    : 6,228,384 B1
DATED         : May 8, 2001
INVENTOR(S)   : Kamezaki et al.

It is certified that error appears in the above-identified patent and that said Letters Patent is hereby corrected as shown below:

Title page,
Item [30], insert
-- [30]   Foreign Application Priority Data
     Apr. 23, 1996 [JP]     Japan…………...137393/1996 --.

Signed and Sealed this

Twenty-ninth Day of October, 2002

Attest:

Attesting Officer

JAMES E. ROGAN
Director of the United States Patent and Trademark Office